United States Patent [19]

Palmer et al.

[11] Patent Number: 5,445,951
[45] Date of Patent: Aug. 29, 1995

[54] REGIOSELECTIVE ENZYMATIC DEACYLATION OF SUCROSE ESTERS IN ANHYDROUS ORGANIC MEDIA

[75] Inventors: David C. Palmer, Clinton, N.J.; Fernand Terradas, Evian-les-Bians, France

[73] Assignee: McNeil-PPC, Inc., Milltown, N.J.

[21] Appl. No.: 133,725

[22] Filed: Oct. 7, 1993

Related U.S. Application Data

[63] Continuation-in-part of Ser. No. 12,182, Feb. 2, 1993, abandoned.

[51] Int. Cl.⁶ ............................................. C12P 19/12
[52] U.S. Cl. .................................. 435/100; 435/196; 435/197; 435/198; 435/219
[58] Field of Search ............... 435/160, 100, 196, 197, 435/198, 219

[56] References Cited

U.S. PATENT DOCUMENTS 5,141,860  8/1992  Bornemann et al. ............... 435/100

FOREIGN PATENT DOCUMENTS 0357476  3/1990  European Pat. Off.
2224504A  5/1990  United Kingdom .
2224733  5/1990  United Kingdom .

OTHER PUBLICATIONS

Ong et al., Preparation of 2,3,6,3',4'-penta-o-acetyl Sucrose, The Precursor of Sucralose, by Enzymatic Methods, Biorganic & Medicinal Chemistry Letters, vol. 2, No. 2, pp. 161-164, 1992.

Chang et al., J. Carbohydrate Chemistry, 10(2), 251-261 (1991).
Chang et al., Carbohydrate Research, 222, 121-129 (1991).
Kloosterman et al., J. Carbohydrate Chemistry, 8(5), 693-704 (1989).
Ong et al., Bioorganic & Medicinal Chemistry Letters, 2(2), 161-164 (1992).
J. S. Dordick, "Designing Enzymes for Use in Organic Solvents", Biotechnol. Prog., 1992, No. 8, 259-267.
A. M. Klibanov, in "Enzymes that work in organic solvents", Chemtech, Jun. 1986, 354-359.
H. M. Sweers et al., J. Am. Chem. Soc., 108, 6421 (1986).
W. J. Hennen et al., J. Org. Chem., 53, 4939 (1988).
J. Zemek et al., Coll. Czech. Chem. Commun., 53, 1851 (1988).
A. Ballesteros et al., *Tetrahedron*, 45, 7077 (1989).
S. Tomic et al., Carbohydrate Res., 210, 191 (1991).
K. Kefurt et al., Carbohydrate Res., 223, 137 (1992).

*Primary Examiner*—Herbert J. Lilling
*Attorney, Agent, or Firm*—Charles J. Metz

[57] ABSTRACT

A process for the preparation of partially acylated derivatives of sucrose by the enzyme catalyzed deacylation of sucrose esters, wherein said process comprises treating a sucrose ester selected from the group consisting of sucrose octaacylate, sucrose heptaacylate, and sucrose hexaacylate in an anhydrous organic medium, with an enzyme or combination of enzymes capable of catalyzing the deacylation of said sucrose ester to produce a partially deacylated sucrose derivative having free hydroxyl group(s) in pre-selected position(s), and recovering the resulting partially deacylated sucrose derivative.

35 Claims, No Drawings

REGIOSELECTIVE ENZYMATIC DEACYLATION OF SUCROSE ESTERS IN ANHYDROUS ORGANIC MEDIA

CROSS-REFERENCE TO RELATED APPLICATION

This application is a continuation-in-part of our application Ser. No. 12,182, filed Feb. 2, 1993, and now abandoned.

The invention relates to the use of enzymes to regioselectively deacylate sucrose esters in anhydrous organic solvents.

BACKGROUND OF THE INVENTION

The artificial sweetener 4,1',6'-trichloro-4,1',6'-trideoxygalactosucrose ("sucralose") is derived from sucrose by replacing the hydroxyls in the 4, 1' and 6' positions with chlorine (In the process of making the sweetener, the stereo configuration at the 4 position is reversed—hence the compound is a galactosucrose.) The direction of the chlorine atoms to only the desired positions is a major synthesis problem because the hydroxyls that are replaced are of differing reactivity; two are primary and one is secondary. The synthesis is further complicated by the fact that the primary hydroxyl in the 6 position is unsubstituted in the final product.

This invention provides an improved route to sucrose esters wherein the ester groups are bonded to predetermined positions on the sucrose molecule. In one aspect, the invention provides an improved route to 4,2,3,3',4'-penta-O-acetylsucrose ("4-PAS") or 6,2,3,3',4'-penta-O-acetylsucrose ("6-PAS") or both, which can be employed to produce sucralose. 4-PAS is readily rearranged to 6PAS, which can be chlorinated and then deacylated to produce sucralose.

BRIEF SUMMARY OF THE INVENTION

The invention provides a process for the preparation of partially acylated derivatives of sucrose by the enzyme catalyzed deacylation of sucrose esters, wherein said process comprises treating a sucrose ester selected from the group consisting of sucrose octaacylate, sucrose heptaacylate, and sucrose hexaacylate in an anhydrous organic medium (as defined herein), with an enzyme or combination of enzymes capable of catalyzing the deacylation of said sucrose ester to produce a partially deacylated sucrose derivative having free hydroxyl group(s) in pre-selected position(s), and recovering the resulting partially deacylated sucrose derivative.

THE PRIOR ART

Bornemann et al., in U.S. Pat. No. 5,141,860 (and in GB 2 224 504 A), disclose a process whereby sucrose octaesters are enzymatically deacylated in aqueous media to produce various partially deacylated sucrose esters.

The preparation of hepta-, hexa-, and/or penta-O-acetylsucroses by enzymatic hydrolysis in aqueous media (which may be biphasic) of octa-O-acetylsucrose is disclosed by Chang et al. in *J. Carbohydrate Chemistry*, 10(2), 251–261 (1991) and in *Carbohydrate Research*, 222, 121–129 (1991); Kloosterman et al., *J. Carbohydrate Chemistry*, 8(5), 693–704 (1989); Mentech et al., EP 0 357 476 (Mar. 7, 1990—equivalent to FR 2 634 497); and Ong et al., *Bioorganic & Medicinal Chemistry Letters*, 2(2), 161–164 (1992).

The following references disclose the regioselective enzymatic deacylation in aqueous media (which may be biphasic) of carbohydrate esters generally:

H. M. Sweers et al., *J. Am. Chem. Soc.*, LOS, 6421 (1986); W. J. Hennen et al., *J. Org. Chem.*, 53, 4939 (1988); J. Zemek et al., *Coil. Czech. Chem. Commun.*, 53, 1851 (1988); A. Ballesteros et al., *Tetrahedron*, 45, 7077 (1989); S. Tomic et al., *Carbohydrate Res.*, 210, 191 (1991); and K. Kefurt et al., *Carbohydrate Res.*, 223, 137 (1992).

J. S. Dordick, in "Designing Enzymes for Use In Organic Solvents" *Biotechnol Prog*, 1992, No 8, 259–267, and A. M. Klibanov, in "Enzymes that work in organic solvents" Chemtech, June 1986, 354–359, discuss potential advantages that can be obtained from the use of enzymes to catalyze reactions in non-aqueous systems.

DETAILED DESCRIPTION OF THE INVENTION

Nomenclature and Abbreviations

As used in this application, the following short names, abbreviations, and terms have the indicated meaning:

Sucralose = 4,1',6'-trichloro-4,1',6'-trideoxygalactosucrose;
SHeptaA = Sucrose Hepta Acetate or hepta-O-acetylsucrose;
SHexaA = Sucrose Hexa Acetate or hexa-O-acetylsucrose;
6-PAS = 6,2,3,3',4'-penta-O-acetylsucrose;
4-PAS = 4,2,3,3',4'-penta-O-acetylsucrose;
4'-OH heptaacetate = 2,3,4,6,1',3',6'-hepta-O-acetylsucrose;
1'-OH heptaacetate = 2,3,4,6,3',4',6'-hepta-O-acetylsucrose;
6'-OH heptaacetate = 2,3,4,6,1',3',4'-hepta-O-acetylsucrose;
1',6'-diOH hexaacetate = 2,3,4,6,3',4'-hexa-O-acetylsucrose;
SOA = sucrose octaacetate;
SOP = sucrose octapropionate;
THF = tetrahydrofuran;
2-methyl THF = 2-methyltetrahydrofuran;
2,5-dimethyl THF = 2,5-dimethyltetrahydrofuran;
2,2,5,5-tetramethyl THF = 2,2,5,5-tetramethyltetrahydrofuran; and
$CCl_4$ = carbon tetrachloride.

As used herein, an "anhydrous" organic medium is intended to mean an organic medium containing not more than about 1 volume percent water, based on the volume of the organic solvent employed in the reaction, and excluding the water bound to the enzyme. Further, when the organic medium is a water-immiscible compound, it is intended that the anhydrous organic media employed in the invention will be monophasic (that is, if there is any water present, the water will not be in sufficient proportion to form an aqueous phase).

The process of the invention comprises treating a sucrose ester selected from the group consisting of sucrose octaacylate, sucrose heptaacylate, and sucrose hexaacylate in an anhydrous organic medium, with an enzyme or combination of enzymes capable of catalyzing the deacylation of said sucrose ester to produce a partially deacylated sucrose derivative having free hydroxyl group(s) in pre-selected position(s), and recovering the resulting partially deacylated sucrose derivative.

Among the sucrose esters that can be used in the process of the invention are sucrose octa-, hepta- and hexaacetate, sucrose octa-, hepta- and hexapropionate, sucrose octa-, hepta- and hexa(n- or secbutyrate), sucrose octa-, hepta- and hexa(α-haloalkanoates) such as sucrose octachloroacetate and sucrose octafluoroacetate, sucrose trihaloalkanoates such as sucrose octa-, hepta- and hexa(trichloroacetate) and sucrose octa-, hepta- and hexa(trifluoroacetate), and other sucrose octa-, hepta- and hexaacylates and haloalkanoates wherein the alkanoate moiety has up to about eight carbon atoms.

The process of the invention employs an organic solvent. The organic solvents, whether used singly or in combination, that have been found to be useful in carrying out the process are toluene, diisopropyl ether, carbon tetrachloride, ethylene glycol dimethyl and diethyl ether, acetonitrile, acetone, THF, cyclohexanone, 2-methyl THF, t-butyl methyl and ethyl ether, 2,5-dimethyl THF, cyclohexanol, n-butyl acetate, t-butyl acetate, 3-heptanone, methyl isobutyl ketone, di-n-propyl ether, butyl ethyl ether, t-amyl methyl ether, chloroform, benzene, anisole, phenetole, hexane, heptane, octane, cyclohexane, di-n-butyl ether, and other cyclic and alicyclic organic solvents including hydrocarbons (both aliphatic and aromatic hydrocarbons), ethers, ketones, esters, alcohols, and halogenated hydrocarbons that will dissolve the sucrose ester substrate employed in the process of the invention. As a class, ethers have proven to be the preferred organic solvents for use in the process of the invention.

In one preferred aspect of the invention, a nucleophile is also employed in the reaction medium. Such nucleophiles include water (for water-immiscible solvents, in an amount less than that which will form a separate aqueous phase in the medium, otherwise in an amount of up to 1 volume percent, based on the volume of the organic solvent), and preferably organic nucleophiles such as alcohols, amines, aminoalcohols, thiols, and oximes. Illustrative examples of such organic nucleophiles include n-butanol, methanol, benzyl alcohol, phenethyl alcohol, diisopropylamine, ethylene glycol, propylene glycol, 2-piperidineethanol, n-butyl thiol, benzyl mercaptan, thiophenol, cystine [3,3'-dithiobis (2-aminopropanoic acid)], acetaldoxime, acetone oxime, and benzaldoxime.

The enzymes that are employed in the invention are hydrolytic enzymes such as lipases, proteases, esterases and amylases. The enzymes are employed to preferentially remove the ester group at preselected positions on the sucrose moiety. In one aspect, the enzyme lipase AY 30 (*Candida cylindracea*) is employed to preferentially remove the ester group primarily at the 4' position, and secondarily at the 1' position. Protease N (*Bacillus subtilis*) is employed to preferentially remove the ester groups at the 1', 4' and 6' positions. Porcine pancreatic lipase is employed to preferentially remove the ester group at the 4' position. Alcalase (*Bacillus licheniformis*) is employed to preferentially remove the ester group at the 1' position and secondarily at the 6' position. Proleather (*Bacillus subtilis*) is employed to preferentially remove the ester group at the 1' position and secondarily at the 6' position. Lipase AP 12 (*Aspergillus niger*) is employed to preferentially remove the ester groups at the 4 and the 6 positions. SP-435 lipase (*Candida antarctica*) is employed to preferentially remove the ester groups primarily at the 6' position and secondarily at the 1' position.

The reaction medium employed in the process of the invention is anhydrous, as defined herein. The small amount of water that may be present is less than that amount that will dissolve the enzyme. It has been found that by carrying out the process of the invention in anhydrous media (as defined herein), the following advantages have been obtained:

1. Increased solubility of the sucrose octaester substrate;
2. Suppression of undesired deacylation;
3. Enhanced regioselectivity of the deacylation reaction;
4. Immobilization of the enzyme is not required, thereby simplifying the process, e.g., the enzyme can be removed from the reaction mixture by simple filtration;
5. Product isolation is easier, e.g., mere evaporation of solvent may be all that is required;
6. Possibility of microbiological contamination is significantly reduced; and
7. Enzymes are more thermally stable in the absence of amounts of water sufficient to dissolve them.

A wide variety of hydrolytic enzymes were initially screened for their ability to regioselectively deacetylate SOA in organic solvents. Among those evaluated in our initial screening experiments, lipase AY 30 showed significant activity. Enzyme activity is dependent upon the presence of a minimum shell of water surrounding the enzyme. The amount of water bound to the enzyme and hence its activity can be regulated by equilibration of the dry enzyme over saturated aqueous salt solutions of known relative humidity (RH). It is known that one way to improve the catalytic power of an enzyme in organic solvent is to use it in the right ionic state. This is generally achieved by lyophilization or precipitation of the enzyme from a buffer at the optimum pH of the enzyme consistent with the general teachings in the art, it was found that when many of the other enzymes were precipitated from pH adjusted buffers (±1 pH unit from the manufacturers' stated optimum pH), significant activity was obtained (see Table 1).

TABLE 1

SOA deacetylation catalyzed by pH precipitated enzymes in diisopropyl ether.

| enzyme | buffer pH[a] | SOA [%][b] | SheptaAs [%][b] | ShexaAs [%][b] |
|---|---|---|---|---|
| lipase CE | 9.0 | 96.5 | 3.5 | 0 |
| lipase AK | 8.0 | 97.2 | 2.8 | 0 |
| protease M | 6.0 | 97.4 | 2.6 | 0 |
| lipase type II | 7.0 | 85.9 | 13.5 | 0.6 |
| lipase MAP 10 | 7.0 | 97.0 | 3.0 | 0 |
| chymotrypsin | 8.0 | 97.5 | 2.5 | 0 |
| PC lipase | 5.0 | 95.2 | 4.5 | 0.3 |
| lipase AP 12 | 6.0 | 76.5 | 21.5 | 2.0 |
| alcalase | 9.0 | 49.4 | 39.7 | 10.9 |
| protease N | 7.0 | 88.1 | 11.1 | 0.8 |
| preleather | 10.0 | 70.6 | 25.9 | 3.5 |
| MM lipase | 10.0 | 94.7 | 5.2 | 0 |
| protease type XXIII | 8.0 | 95.2 | 4.8 | 0 |

[a]The buffer pH listed is the optimal pH for enzyme activity in anhydrous solvents.
[b]The product distribution was obtained by HPLC analysis after 24 hrs incubation.

For several of the enzymes that had been identified as being active, experiments were undertaken to evaluate their activity in different solvents. Identical enzyme catalyzed SOA deacetylations were run in numerous anhydrous solvents. After 24 hrs incubation an aliquot was analyzed by HPLC. The results of these solvent experiments are displayed in Tables 2–5, and clearly show that the solvent has a marked effect on the activity of each enzyme evaluated.

TABLE 2

Effect of the solvent on lipase AY 30 SOA deacetylation.

| solvent | log P[a] | SOA [%][b] | SheptaA [%][b] | ShexaA [%][b] |
|---|---|---|---|---|
| acetonitrile | — 0.33 | 98.6 | 1.4[c] | 0 |
| acetone | — 0.23 | 98.6 | 1.4[c] | 0 |
| THF | 0.49 | 98.7 | 1.3[c] | 0 |
| ethylene glycol diethyl ether | 0.87[d] | 85.0 | 13.5 | 1.5 |
| cyclohexanone | 0.96 | 97.5 | 2.5 | 0 |
| 2-methyl THF | 1.0[e] | 96.2 | 3.8 | 0 |
| t-butyl methyl ether | 1.3 | 61.6 | 28.8 | 9.6 |
| 2,5-dimethyl THF | 1.5[e] | 96.2 | 3.8 | 0 |
| cyclohexanol | 1.5 | 96.8 | 2.9 | 0.3 |
| n-butyl acetate | 1.7 | 95.2 | 4.6 | 0.4 |
| 3-heptanone | 1.8 | 85.1 | 14.9 | ?[f] |
| dipropyl ether | 1.9 | 51.6 | 32.4 | 16.0 |
| butyl ethyl ether | 1.9 | 73.9 | 21.4 | 4.7 |
| t-amyl methyl ether | 1.9 | 45 | 37.1 | 17.9 |
| t-butyl ethyl ether | 1.9 | 40.8 | 38.1 | 21.1 |
| diisopropyl ether | 1.9 | 29.6 | 39.6 | 30.9 |
| chloroform | 2.0 | 86.7 | 11.6 | 1.7 |
| benzene | 2.0 | 97.9 | 1.7 | 0.4 |
| anisole | 2.1 | 86.1 | 9.6 | 4.3 |
| 2,2,5,5-tetramethyl THF | 2.5[e] | 68.4 | 31.6 | ?[f] |
| heptanol | 2.5 | 93.4 | 6.0 | 0.6 |
| toluene | 2.5 | 78.7 | 16.5 | 4.8 |
| CCl4 | 3.0 | 86.9 | 10.4 | 2.7 |

[a]log P is a measurement of the solvent hydrophobicity (logarithm of the solvent partition coefficient between n-octanol and water [Rekker, "The Hydrophobic Fragmental Constant", Elsevier, Amsterdam (1977)]). The log P values from this table are from Laane et al., Biotechnol Bioeng. 30,81 (1987).
[b]The product distribution was obtained by HPLC analysis after 24 hrs incubation.
[c]The sucrose heptaacetates detected are due to a minor impurity in the SOA.
[d]Estimated from known log P values for ethanol, diethyl ether and ethoxyethanol.
[e]Estimated by incremental addition of 0.5 unit per methyl group to the log P value for THF.
[f]This value is not reported because other peaks, probably from the solvent, interfere with the sucrose hexaacetate peak.

TABLE 3

Solvent effect on alcalase catalyzed deacetylation of SOA.

| solvent | log P[a] | SOA [%][b] | SheptaA [%][b] | ShexaA [%][b] |
|---|---|---|---|---|
| THF | 0.49 | 98.0 | 2.0 | 0 |
| t-butyl methyl ether | 1.3 | 92.6 | 6.8 | 0.6 |
| n-butyl acetate | 1.7 | 97.6 | 2.4 | 0 |
| dipropyl ether | 1.9 | 83.9 | 14.5 | 1.6 |
| butyl ethyl ether | 1.9 | 81.4 | 16.9 | 1.7 |
| diisopropyl ether | 1.9 | 75.2 | 22.3 | 2.5 |
| benzene | 2.0 | 93.3 | 6.7 | 0 |
| anisole | 2.1 | 96.1 | 3.9 | 0 |
| toluene | 2.5 | 93.8 | 6.0 | 0.2 |
| CCl4 | 3.0 | 94.8 | 5.2 | 0 |

[a]log P is a measurement of the solvent hydrophobicity (logarithm of the solvent partition coefficient between n-octanol and water). The log P values from this table are from Laane et al.
[b]The product distribution was obtained by HPLC analysis after 24 hrs incubation. Two sucrose heptaacetates were detected, 1'-OH and 6'-OH (R$_f$: 7.7 and 8.5 min.), the peak areas were added and used to obtain the total % of heptaacetates.

TABLE 4

Solvent effect on lipase AP 12 catalyzed deacetylation of SOA.

| solvent | log P[a] | SOA [%][b] | SheptaA [%][b] | ShexaA [%][b] |
|---|---|---|---|---|
| THF | 0.49 | 98.4 | 1.6 | 0 |
| n-butyl acetate | 1.7 | 97.6 | 2.4 | 0 |
| dipropyl ether | 1.9 | 81.8 | 15.9 | 2.3 |
| butyl ethyl ether | 1.9 | 81.6 | 16.3 | 2.1 |
| diisopropyl ether | 1.9 | 82.7 | 15.7 | 1.6 |
| benzene | 2.0 | 96.6 | 3.4 | 0 |
| anisole | 2.1 | 96.2 | 3.8 | 0 |
| toluene | 2.5 | 94.2 | 5.8 | 0 |
| CCl4 | 3.0 | 95.1 | 4.3 | 0.6 |

[a]log P is a measurement of the solvent hydrophobicity (logarithm of the solvent partition coefficient between n-octanol and water). The log P values from this table are from Laane et al.
[b]The product distribution was obtained by HPLC analysis after 24 hrs incubation. One sucrose heptaacetate (R$_f$: 8.1 min.) was detected.

TABLE 5

Solvent effect on proleather catalyzed deacetylation of SOA.

| solvent | log P[a] | SOA [%][b] | SheptaA [%][b] | ShexaA [%][b] |
|---|---|---|---|---|
| THF | 0.49 | 97.4 | 2.6 | 0 |
| t-butyl methyl ether | 1.3 | 72.4 | 24.4 | 3.2 |
| n-butyl acetate | 1.7 | 81.3 | 16.5 | 2.2 |
| dipropyl ether | 1.9 | 75.2 | 21.5 | 3.3 |
| t-butyl ethyl ether | 1.9 | 97.2 | 2.8 | 0 |
| diisopropyl ether | 1.9 | 70.6 | 25.9 | 3.5 |
| benzene | 2.0 | 84.8 | 13.9 | 1.4 |
| anisole | 2.1 | 79.2 | 19.4 | 1.4 |
| toluene | 2.5 | 82.8 | 15.2 | 2.0 |
| CCl4 | 3.0 | 89.1 | 9.6 | 1.3 |

[a]log P is a measurement of the solvent hydrophobicity (logarithm of the solvent partition coefficient between n-octanol and water). The log P values from this table are from Laane et al.
[b]The product distribution was obtained by HPLC analysis after 24 hrs incubation. Two sucrose heptaacetates were detected, 1'-OH and 6'-OH (R$_f$: 7.7 and 8.5 min.), the peak areas were added and used to obtain the total % of heptaacetates.

Solvent effect on immobilized hydrolytic enzymes.

Alcalase and lipase AY 30 were deposited on Hyflo Super Cell and used as catalysts for SOA deacetylation reactions in several anhydrous solvents. With both immobilized enzymes (Tables 6 and 7) advantageous solvent effects were observed.

TABLE 6

Solvent effect on alcalase deposited on Hyflo Super Cell catalyzed deacetylation of SOA.

| solvent | log P[a] | SOA [%][b] | SheptaA [%][b] | ShexaA [%][b] |
|---|---|---|---|---|
| THF | 0.49 | 97.3 | 2.7 | 0 |
| t-butyl methyl ether | 1.3 | 97.3 | 2.7 | 0 |
| t-butyl acetate | 1.7 | 98.2 | 1.8 | 0 |
| dipropyl ether | 1.9 | 92.9 | 6.5 | 0.6 |
| butyl ethyl ether | 1.9 | 97.8 | 2.2 | 0 |
| diisopropyl ether | 1.9 | 89.3 | 9.9 | 0.8 |
| benzene | 2.0 | 97.9 | 2.1 | 0 |
| anisole | 2.1 | 98.0 | 2.0 | 0 |
| toluene | 2.5 | 97.8 | 2.2 | 0 |
| CCl4 | 3.0 | 98.6 | 1.4 | 0 |

[a]log P is a measurement of the solvent hydrophobicity (logarithm of the solvent partition coefficient between n-octanol and water). The log P values from this table are from Laane et al.
[b]The product distribution was obtained by HPLC analysis after a 4 hour incubation. Two sucrose heptaacetates were detected, 1'-OH and 6'-OH (R$_f$: 7.7 and 8.5 min.), the peak areas were added and used to obtain the total % of heptaacetates.

TABLE 7

Solvent effect on lipase AY 30 deposited on Hyflo Super Cell catalyzed deacetylation of SOA.

| solvent | log P[a] | SOA [%][b] | SheptaA [%][b] |
|---|---|---|---|
| THF | 0.49 | 98. | 2.0 |
| t-butyl methyl ether | 1.3 | 96.0 | 4.0 |
| n-butyl acetate | 1.7 | 97.6 | 2.4 |
| dipropyl ether | 1.9 | 93.4 | 6.6 |
| butyl ethyl ether | 1.9 | 96.0 | 4.0 |
| diisopropyl ether | 1.9 | 85.7 | 14.3 |
| benzene | 2.0 | 97.9 | 2.1 |
| anisole | 2.1 | 98.2 | 1.2 |
| toluene | 2.5 | 94.5 | 5.5 |
| CCl$_4$ | 3.0 | 97.5 | 2.5 |

[a]log P is a measurement of the solvent hydrophobicity (logarithm of the solvent partition coefficient between n-octanol and water). The log P values from this table are from Laane et al.
[b]The product distribution was obtained by HPLC analysis after 24 hrs incubation.

Regiochemistry for SOA deacetylation by hydrolytic enzymes.

An important aspect of this work was to assign, unequivocally, the structures of all sucrose hepta-, hexa-, and pentaacetates obtained by enzymatic deacetylation of SOA. These structures were assigned by perdeuterioacetylation followed by $^1$H-NMR, as described by Rathbone E. B., Carbohydr. Res., 205,402 (1990). From examination of the results in Table 8 (below) using lipase AY 30 and lipase type II the primary deacetylation product is the 4'- OH heptaacetate. In contrast, the proteases alcalase and proleather effect deacetylation primarily at 1'- position with some reaction occurring at the 6'- position. Deacetylation using lipase AP 12 generates both the 4- and 6-OH heptaacetates, whereas the SP-435 lipase from *Candida antarctica* produces mainly the 6'-OH heptaacetate together with the 1'-OH heptaacetate. Finally, protease N generates a nearly equimolar mixture of 1'- 4'- and 6'- OH heptaacetates

TABLE 8

Activity and regioselectivity of enzymes for SOA deacetylation.

| enzyme[a] | buffer pH[b] | % conv[c] | regiochemistry[d] | | | | |
|---|---|---|---|---|---|---|---|
| | | | 1'OH | 4'OH | 6'OH | 4OH | 6OH |
| lipase AY 30 | | 70.4 | 12 | 36 | 1 | | |
| SP-435 lipase | | 17.7 | 2 | 3 | 15 | | |
| protease N[e] | 7.0 | 12.9 | 9 | 8 | 9 | | |
| lipase type II | 7.0 | 14.1 | | 1 | 1 | | |
| alcalase | 9.0 | 28.1 | 13 | | 2 | | |
| proleather | 10.0 | 29.4 | 19 | 5 | 4 | | |
| lipase AP 12 | 6.0 | 23.5 | | | 1 | 10 | 12[f] |

[a]Other pH optimized enzymes were tested for SOA deacetylation with a conversion <6%: lipase CE, 9.0; lipase AK, 8.0; protease M. 6.0; lipase MAP 10, 7.0; chymotrypsin, 8.0; PC lipase, 5.0; MM lipase, 10.0; protease type XXII, 8.0.
[b]Where the pH is indicated in this column, the enzymes were precipitated from a buffer at the indicated pH. The buffer pH is the optimal pH found for enzyme activity in anhydrous diisopropyl ether.
[c]The % conversion is the total of all sucrose hepta- and hexa- acetates. No deacetylation occurred in absence of enzymes.
[d]The sucrose heptaacetate structure of each enzymatic reaction was assigned by 1H-NMR after perdeuterioacetylation of the molecule. For quantification purposes the HPLC sucrose heptaacetate peak height was used in this table.
[e]The regiochemistry for the products of the protease N catalyzed reaction was assigned on the basis of the HPLC retention time.
[f]The structure of the 2,3,4,1',3',4',6'-hepta-O-acetyl sucrose was deduced from the following fact. Two sucrose heptaacetates were detected by HPLC during the incubation but after column chromatography only the 2,3,6,1',3',4',6'-hepta-O-acetyl was obtained. Acetyl migration from the 4 to 6 position, known to be a facile process, probably occurs during the purification.

Nucleophile selection and concentration effects.

Identical SOA deacetylations catalyzed by alcalase, proleather or lipase AP 12, were carried out in presence of several nucleophiles, the results of which are shown in Table 9. In the alcalase catalyzed reaction, significantly greater conversions (at least 25% increase relative to the reaction with no added nucleophile) were achieved by using methanol or diisopropylamine as the nucleophile, while in the proleather catalyzed reaction, all added nucleophiles except cyclohexanol, diisopropylamine and tetramethylpiperidine yielded similar improvement. The reaction catalyzed by lipase AP 12 showed modest improvement in conversion in the presence of a nucleophile.

TABLE 9

Nucleophile screening for alcalase, proleather and lipase AP 12 catalyzed deacetylation of SOA in diisopropyl ether.

| | alcalase | | proleather | | lipase AP 12 |
|---|---|---|---|---|---|
| nucleophile[a] | % conv[b] | regiochem[c] | % conv[b] | regiochem[c] | % conv[b] |
| none | 28.1 | 7.3 | 33.6 | 3.8 | 23.9 |
| methanol | 38.8 | 8.6 | 53.8 | 8.4 | 28.2 |
| ethanol | 31.8 | 7.5 | 47.7 | 5.6 | 26.7 |
| propanol | 29.7 | 8.8 | 46.4 | 5.3 | 26.2 |
| butanol | 28.7 | 7.4 | 44.4 | 4.8 | 25.7 |
| benzyl alcohol | 26.8 | 8.1 | 46.8 | 6.6 | 22.5 |
| cyclohexanol | 24.7 | 8.0 | 38.2 | 3.9 | 25.0 |
| cyclohexylmethanol | 28.0 | 8.1 | 42.8 | 4.4 | 24.8 |
| phenethyl alcohol | 28.7 | 7.3 | 51.5 | 5.3 | 25.7 |
| 2-piperidineethanol | 30.4 | 8.6 | 41.3 | 5.1 | 10.4 |
| diisopropylamine | 37.9 | 9.5 | 37.3 | 4.9 | 3.2 |
| tetramethylpiperidine | 29.4 | 6.0 | 32.9 | 4.4 | 0[d] |

[a]The nucleophile concentration used throughout this experiment is 200 mM. No SOA deacetylation occurred in absence of the enzymes.
[b]The * conversion (66 hrs incubation) is represented by the sum of the sucrose heptaacetates obtained compared to the residual SOA.
[c]The alcalase and proleather regiochemistry is defined as the peak height of the 2,3,4,6,3',4',6'-hepta-O-acetyl sucrose divided by the peak height of the 2,3,4,6,1',3',4'-hepta-O-acetyl sucrose.
[d]No reaction occurred.

As shown in Table 10, modest enhancements in overall conversion were achieved in the alcalase and lipase AP 12 catalyzed reactions at 0.5 and 1.0M methanol, respectively. In the proleather catalyzed reaction, a striking 120% increase in conversion was obtained using 1.0M methanol. Similar results were obtained using 1.0M n-butanol or phenethyl alcohol.

TABLE 10

Effect of the methanol concentration on alcalase, proleather and lipase AP 12 catalyzed deacetylation of SOA in diisopropyl ether.

| | alcalase | | proleather | | lipase AP 12 |
|---|---|---|---|---|---|
| methanol conc. [mM] | % conv[b] | regiochem[b] | % conv[a] | regiochem[c] | % conv[a] |
| 0 | 25.9 | 6.9 | 32.2 | 3.8 | 22.3 |
| 20 | 28.7 | 7.4 | 38.1 | 4.8 | 22.4 |
| 50 | 31.5 | 8.3 | 41.2 | 5.9 | 23.5 |
| 100 | 34.2 | 8.1 | 44.6 | 6.6 | 25.7 |
| 200 | 35.0 | 8.6 | 49.4 | 7.9 | 24.0 |
| 500 | 35.5 | 8.2 | 65.4 | 12.4 | 31.3 |
| 1000 | 21.4 | 5.6 | 71.1 | 12.6 | 33.4 |

TABLE 10-continued

Effect of the methanol concentration on alcalase, proleather and lipase AP 12 catalyzed deacetylation of SOA in diisopropyl ether.

| methanol conc. [mM] | alcalase | | proleather | | lipase AP 12 |
|---|---|---|---|---|---|
| | % conv$^b$ | regio-chem$^b$ | % conv$^a$ | regio-chem$^c$ | % conv$^a$ |
| 2000 | -12.3 | 7.1 | 66.8 | 11.5 | 21.3 |

$^a$The % conversion (66 hrs incubation) is represented by the sum of the sucrose heptaacetates obtained compared to the residual SOA.
$^b$The alcalase and proleather regiochemistry is defined as the peak height of the 2,3,4,6,3',4',6'-hepta-O-acetyl sucrose divided by the peak height of the 2,3,4,6,1',3',4'-hepta-O-acetyl sucrose.

In one preferred aspect of the invention, a combination of the enzymes displayed above in Table 8 are used to prepare 4-PAS and/or 6-PAS by the concurrent or sequential treatment of SOA by a combination of these enzymes appropriate to deacetylate the ester groups on the 4-, 1'- and 6'- positions or on the 6-, 1'- and 6'-positions of the SOA.

Synthesis of 6-PAS by Alcalase or Alcalase/lipase AP12 catalyzed deacetylation of SOA in diisopropyl ether A large scale alcalase catalyzed SOA deacetylation reaction was performed. (Details are presented below in the experimental section.) After 5 days incubation the alcalase was removed by filtration. The SOA deacetylation products were separated by silica gel chromatography and the structure assignments made using the perdeuterioacetylation technique. A 1 to 7 mixture of 2,3,4,6,1',3',4'-hepta-O-acetyl sucrose and 2,3,4,6,3',4',6'-hepta-O-acetyl sucrose; 2,3,4,6,3',4'-hexa-O-acetyl sucrose; and 6-PAS were obtained in 30%, 7% and 0.5% yield, respectively. Alternatively, 4-PAS and/or 6-PAS can be obtained by deacylating the 2,3,4,6,3',4'-hexa-O-acetyl sucrose using lipase AP 12. The resulting sucrose pentaacetate (97% pure by HPLC) was identified by perdeuterioacetylation technique as 6-PAS (yield: 11%).

Synthesis of 6-PAS by proleather catalyzed deacetylation of SOA in diisopropyl ether containing methanol.

A large scale proleather catalyzed SOA deacetylation reaction was performed using 1.0M methanol as the nucleophile. (Details are presented below in the experimental section.) After 5 days incubation the proleather was removed by filtration. The SOA deacetylation products were separated by silica gel chromatography and the structure assignments made using the perdeuterioacetylation technique. A 1 to 7 mixture of 2,3,4,6,1',3',4'-hepta-O-acetyl sucrose and 2,3,4,6,3',4',6'-hepta-O-acetyl sucrose; 2,3,4,6,3',4'-hexa-O-acetylsucrose; and 6-PAS were obtained in 48%, 17% and 2% yield, respectively.

Enzyme screening for SOP deacylation.

To extend the scope and utility of this study, sucrose octapropionate was synthesized and used as substrate in enzyme catalyzed deacylation reactions. One important advantage conferred by SOP versus SOA is significantly enhanced solubility in more hydrophobic solvents, e.g., hexane, cyclohexane, heptane, octane, and the like. The hydrolytic enzymes were screened for their capability to deacylate SOP in heptane with n-butanol as the nucleophile. After 24 hrs incubation aliquots were analyzed by HPLC. As is shown in Table 11, numerous hydrolytic enzymes effected deacylation of SOP. In one interesting example, HPLC co-injection of the heptapropionates obtained from lipase AY 30 and protease type XXIII showed two distinct compounds, confirming different enzymatic regioselectivity.

TABLE 11

SOP hydrolytic enzyme screen in heptane with n-butanol.

| enzyme$^a$ | BuOpropionate$^b$ [cAUs]$^c$ | SOP [%]$^d$ | SheptaP's | | | |
|---|---|---|---|---|---|---|
| | 4.9$^e$ | 21.2 | 7.0 | 8.2 | 8.8 | 9.2 | 9.6 |
| protease N | | 99.1 | | 0.9 | | | |
| protease M | 183 | 95.1 | | 3.4 | | 1.5 | |
| lipase type I | | 97.5 | | 2.3 | | 0.2 | |
| chymotrypsin | | 96.1 | | 3.9 | | | |
| protease type XIII | | 94.3 | | 5.4 | | 0.3 | |
| phosphatase acid | | 98.4 | | 1.6 | | | |
| lipase AY 30 | 6435 | 85.7 | | 9.7 | | 4.6 | |
| lipase GC 4 | | 98.9 | | 1.1 | | | |
| lipase L 10 | | 97.9 | | 2.1 | | | |
| lipase R 10 | | 98.2 | | 1.8 | | | |
| lipase type II | 59 | 98.1 | | 1.7 | | 0.2 | |
| lipase N | | 99.3 | | 0.7 | | | |
| protease B | | 98.8 | | 1.2 | | | |
| peptidase A | 51 | 98.5 | | 0.9 | | 0.6 | |
| protease PZT | 80 | 97.9 | | 1.7 | 0.4 | | |
| lipase type VII | 4731 | 93.6 | | 3.3 | 0.3 | 2.8 | |
| protease type XIX | | 99.0 | | 0.8 | 0.2 | | |
| lipase AP 12 | 84 | 97.4 | | 1.6 | 0.1 | 0.9 | |
| lipase AK | | 98.8 | | 1.0 | | 0.2 | |
| lipase MAP 10 | 89 | 98.2 | | 1.8 | | | |
| newlase A | | 98.6 | | 1.0 | | 0.4 | |
| protease 2A | 138 | 97.5 | | 1.2 | 0.2 | 1.1 | |
| lipase CE | 130 | 97.0 | 0.4 | 1.3 | 0.5 | 0.4 | 0.4 |
| newlase II | | 98.9 | | 0.9 | | 0.2 | |
| lipase PGE | | 98.9 | | 1.1 | | | |
| protease type XXIII | 298 | 94.2 | | 0.8 | 4.4 | | 0.6 |
| bromelaine | | 99.0 | | 0.7 | | | 0.3 |
| papaine | | 98.8 | 0.3 | 0.9 | | | |
| MM lipase | 173 | 97.1 | | 1.0 | | 0.2 | 0.9 |
| CV lipase | | 99.5 | | 0.5 | | | |
| stachyase | 78 | 98.3 | | 0.8 | | 0.2 | 0.7 |
| biozyme S | 135 | 96.4 | | 0.7 | | 1.8 | 1.1 |
| PLE-A | | 99.2 | | 0.8 | | | |
| LPL-80 | | 99.3 | | 0.7 | | | |
| RA lipase | | 99.3 | | 0.7 | | | |
| PC lipase | 146 | 98.2 | 0.2 | 0.7 | | 0.2 | 0.7 |
| proleather | 180 | 96.8 | | 0.9 | 1.6 | 0.2 | 0.5 |

$^a$Further detail can be found in the experimental section.
$^b$Butyl propionate formed by the reaction of butanol with the acylenzyme.
$^c$cAUs is the peak area expressed in absorbance units divided by 100.
$^d$The product distribution was obtained by HPLC analysis.
$^e$The values in this row are HPLC retention times in minutes.

Solvent effect on lipase AY 30 and protease type XXIII catalyzed deacylation of SOP Identical SOP deacylations were performed with lipase AY 30 or protease type XXIII in numerous anhydrous organic solvents, as shown in Tables 12 and 13. As with SOA, enzymatic deacylation of SOP showed pronounced solvent effects with good conversions possible in a variety of solvents, including very hydrophobic ones, such as hexane, heptane and octane.

TABLE 12

Effect of the solvent on lipase AY 30 catalyzed deacylation of SOP.

| solvent | log P$^a$ | SOA [%]$^b$ | SheptaP's [%]$^b$ | | | ShexaP [%]$^b$ |
|---|---|---|---|---|---|---|
| | | 21.4$^c$ | 8.2 | 8.9 | 9.4 | 4.2 |
| acetonitrile | -0.33 | 98.7 | 1.1 | 0 | 0.2 | 0 |
| acetone | -0.23 | 98.7 | 1.2 | 0 | 0.1 | 0 |
| butanone | 0.29 | 98.9 | 0.9 | 0 | 0.2 | 0 |

TABLE 12-continued

Effect of the solvent on lipase AY 30 catalyzed deacylation of SOP.

| solvent | log P[a] | SOA [%][b] | SheptaP's [%][b] | | ShexaP [%][b] |
|---|---|---|---|---|---|
| THF | 0.49 | 98.0 | 1.6 | 0 | 0.1 | 0.3 |
| cyclohexanone | 0.96 | 98.8 | 0.9 | 0 | 0.3 | 0 |
| t-BuOMe | 1.3 | 88.7 | 4.3 | 0.3 | 5.9 | 0.8 |
| n-BuOAc | 1.7 | 97.9 | 1.4 | 0 | 0.7 | 0 |
| 3-heptanone | 1.8 | 93.0 | 3.3 | 0.8 | 2.9 | 0 |
| diisopropyl ether | 1.9 | 54.7 | 17.3 | 1.5 | 13.5 | 13.0 |
| heptanol | 2.5 | 97.9 | 1.4 | 0 | 0.7 | 0 |
| toluene | 2.9 | 97.3 | 1.3 | 0 | 1.2 | 0.2 |
| dibutyl ether | 2.9 | 70.5 | 12.3 | 1.1 | 7.9 | 8.2 |
| octanol | 3.0 | 97.1 | 1.8 | 0 | 1.1 | 0 |
| CCl$_4$ | 3.1 | 98.2 | 1.1 | 0 | 0.7 | 0 |
| cyclohexane | 3.2 | 86 | 5.6 | 0.4 | 5.2 | 2.8 |
| hexane | 3.5 | 79.3 | 8.6 | 0.6 | 5.7 | 5.8 |
| dipentyl ether | 3.9 | —[d] | — | — | — | — |
| heptane | 4.0 | 79.6 | 8.9 | 0.5 | 4.4 | 6.6 |
| octane | 5.0 | 80.0 | 8.9 | 0.5 | 2.9 | 7.7 |

[a]log P is a measurement of the solvent hydrophobicity (logarithm of the solvent partition coefficient between n-octanol and water). The log P values from this table are from Laane et al.
[b]The product distribution was obtained by HPLC analysis.
[c]The values in this row are HPLC retention times in minutes.
[d]These values could not be determined because other peaks interfered with the sucrose hepta- and hexapropionate peaks.

TABLE 13

Effect of the solvent on protease type XXIII catalyzed deacylation of SOP.

| solvent | log P[a] | SOP [%][b] | SheptaP's [%][b] | | |
|---|---|---|---|---|---|
| | | 21.4[c] | 8.3 | 8.9 | 9.9 |
| acetonitrile | −0.33 | 98.4 | 1.1 | 0 | 0.5 |
| acetone | −0.23 | 99.1 | 0.7 | 0 | 0.2 |
| butanone | 0.29 | 98.8 | 1.0 | 0 | 0.2 |
| THF | 0.49 | [b]The * conversion (66 hrs incubation) is represented by the sum of the sucrose heptaacetates obtained compared to the residual SOA. | | | |

[c]The alcalase and proleather regiochemistry is defined as the peak height of the 2,3,4,6,3',4',6'-hepta-O-acetyl sucrose divided by the peak height of the 2,3,4,6,1',3',4'-hepta-O-acetyl sucrose.
[d]No reaction occurred.

pH precipitated hydrolytic enzymes for SOP deacetylation.

To increase the number and/or activities of enzymes active with SOP, pH precipitation experiments, as described for SOA, were undertaken. Several additional enzymes were found capable of deacetylating SOP, for example, lipase AP 12, alcalase, proleather, protease N, lipase type II, and MM lipase. These latter enzymes deacylated both SOA and SOP. The results of these experiments are displayed in Table 14.

TABLE 14

SOP deacylation catalyzed by pH precipitated enzymes in diisoprodyl ether.

| enzyme | buffer pH[a] | SOP [%][b] | SheptaP's [%][b] | ShexaP's [%][b] |
|---|---|---|---|---|
| lipase CE | 9.0 | 97.9 | 2.1 | 0 |
| lipase AK | 8.0 | 98.2 | 1.8 | 0 |
| protease M | 6.0 | 97.8 | 2.2 | 0 |
| lipase type II | 7.0 | 96.5 | 3.5 | 0 |
| lipase MAP 10 | 9.0 | 99.1 | 0.9 | 0 |
| chymotrypsin | 8.0 | 98.2 | 1.8 | 0 |
| lipase AP 12 | 5.0 | 93.7 | 5.9 | 0.4 |
| alcalase | 9.0 | 81.8 | 15.9 | 2.3 |
| protease N | 7.0 | 86.6 | 11.1 | 2.0 |
| proleather | 10.0 | 93.2 | 6.8 | 0 |
| MM lipase | 10.0 | 95.7 | 4.3 | 0 |
| protease type XXIII | 8.0 | 79.1 | 13.9 | 6.2 |

[a]The buffer pH listed is the optimal pH for enzyme activity in anhydrous media.
[b]The product distribution was obtained by HPLC analysis after 24 hrs incubation.

EXPERIMENTAL

The following enzymes were obtained from Amano: lipase AP 12 (*Aspergillus niger*, 125 U/mg), lipase AY 30 (*Candida cylindracea*, 34 U/mg), lipase GC 4 (*Geotrichum candidum*, 4.4 U/mg), lipase AK (*Pseudomonas sp.*, 22 U/mg), lipase CE (*Humicolosa langinosa*, 11 U/mg), lipase N (*Rhizopus niveus*, 80 u/mg), lipase L 10 (*Candida lypolitica*, 11 U/mg), lipase MAP 10 (*Mucor javanicus*, 10.6 U/mg), lipase PGE (calf tongue root and salivary gland, 0.7 U/mg), lipase R 10 (*Penicillium roqueforti*, 10 U/mg), LPL-80 (lipoprotein lipase, 881 U/mg), newlase A (*Aspergillus niger*, 41.8 U/mg), newlase 2 (*Rhizopus niveus*, 15 U/mg), peptidase A (*Aspergillus oryzae*, 10 U/mg), protease 2A (*Aspergillus oryzae*, 22.5 U/mg), protease B (*Penicillium sp.*, 2 U/mg), protease M (*Aspergillus oryzae*, 6 U/mg), protease N (*Bacillus subtilis*, 186 U/mg), proleather (*Bacillus subtilis*, 10.5 U/mg), protease PZT (porcine pancreas and *Aspergillus*, 54 U/mg), stachyase (*Aspergillus niger*, 0.3 U/mg), PLE-A (porcine liver, 5.2 U/mg), biozyme S (fungal amylase, 64 U/mg); from Sigma: lipase type I (wheat germ, 9.6 U/mg), lipase type II (porcine pancreas, 50 U/mg), protease type XIII (*Aspergillus saitoi*, 0.4 U/mg), protease type XIX (*Aspergillus sojae*, 0.44 U/mg), protease type XXIII (*Aspergillus oryzae*, 3.5 U/mg), chymotrypsin (bovine pancreas, 48 U/mg), papain (Papaya latex, 2.8 U/mg), bromelain (pineapple stem, 22.9 U/mg), phosphatase acid (wheat germ); from Biocatalysts: MM lipase (Mucor miehei, 17 U/mg), CV lipase (*Chromobacterium viscosum*, 25 U/mg), PC lipase (*Penicillium cyclopium*, 1.25 U/mg), RA lipase (*Rhizopus arrhizus*, 3.5 U/mg), PF lipase (*Pseudomonas fluorescens*, 14.5 U/mg). Neutrase, SP-435 lipase (*Candida antarctica*, 7 PLU/mg) and alcalase (*Bacillus licheniformis*) were gifts from Novo Nordisk.

Hyflo Super Cell and silica gel (70–230 mesh) were obtained from Fluka AG. All other chemicals were of the highest grade and were purchased from Aldrich.

Organic solvents employed in this work were either purchased as anhydrous or stored over 3 Å molecular sieves. All buffers used in this work were prepared following the procedures described in the Practical Handbook of Biochemistry and Molecular Biology (For pH 10 and 9 a glycine—NaOH buffer was used, for pH 8 and 7 a sodium phosphate buffer and for pH 6, 5 and 4 a citrate—phosphate buffer).

HPLC analysis. Routine screening was performed on a Supelcosil LC-18-DB column (150×4.6 mm, 5μ) using an isocratic mode with either acetonitrile/water (35/65) or acetonitrile/water (60/40) as eluant for reactions involving sucrose octaacetate (SOA) and sucrose octapropionate (SOP), respectively. All flow rates were 1.0 ml/min with UV detection at 220 nm. To identify all products from SOA deacetylation, a gradient mode was employed using 15% to 35% acetonitrile in water over 40 minutes followed by 35/65 acetonitrile/water isocratic elution for 20 minutes. To screen nucleophiles for SOA deacetylation, an isocratic elution mode was employed using 30/70 acetonitrile/water for 16 min followed by a gradient from 30% to 35% acetonitrile in water over 5 min and finally isocratic elution using 35/65 acetonitrile/water for 16 min. To assess the enzyme regiochemistry for SOA deacetylation, an isocratic elution mode was employed using 25/75 acetonitrile/water for 55 minutes.

Identification of the Sucrose Hepta, Hexa or Pentaacetates Obtained Enzymatically. The fraction of sucrose hepta, hexa or pentaacetates were identified as follows. The compound(s) of interest was dissolved in 1.0 ml 99.0 atom % pyridine—$d_5$ followed by addition of 1.0 ml 99 +atom % acetic anhydride—$d_6$. The resulting solution was shaken at 45° C. and 300 RPM for several hours until TLC analysis (silica gel, 9/1 $CHCl_3$/MeOH) indicated complete reaction. The reaction mixture was evaporated in vacuo and the residue washed several times with water to remove residual pyridine-$d_5$ and/or acetic anhydride-$d_6$. The resulting oily solid was dissolved in 5 ml off chloroform and passed through Whatmann 12.5 cm 1 PS silicone treated filter paper to remove water. After-evaporation of the chloroform the residue was dissolved in 1/1 pyridine-$d_5$/benzene-$d_6$ for $^1$H-NMR analysis.

Enzyme Precipitation. Alcalase was prepared by adding 37.5 ml cold acetone ($-20°$ C.) to 25 ml of alcalase solution as supplied by Novo. The aqueous acetone was decanted and the residue dissolved in 25 ml of pH 9.0 glycine—NaOH buffer. The pH of this solution was adjusted to 9.0 with a few drops of dilute NaOH solution. Cold acetone (37.5 ml at $-20°$ C.) was added to the buffered alcalase solution and the precipitate collected by filtration on a medium porosity glass funnel and dried overnight at 2 millitorr. The resulting pellet was ground to a fine powder and stored at 4° C. over saturated aqueous potassium carbonate (RH: 43%) for 24 hrs.

The pH of commercial powdered enzymes was adjusted in the following way: The enzyme (3 g) was dissolved in 25 ml of an appropriate buffer and the pH adjusted with dilute NaOH or citric/phosphoric acid solution. Cold acetone (37.5 ml at $-20°$ C.) was added and the precipitate collected on a medium porosity glass funnel and dried overnight at 2 millitorr. The protein pellet was ground to a fine powder and equilibrated at 4° C. over saturated aqueous potassium carbonate (RH: 43%) for 24 hrs.

Enzyme immobilization. The pH of a solution of 900 mg of buffered alcalase in 18 ml of water was adjusted to 9.0 with dilute NaOH. Hyflo super cell (6 g) was added and the slurry thoroughly mixed. The mixture was dried in vacuo at 2 millitorr overnight and stored over saturated aqueous ammonium sulfate solution (RH: 82%) for 24 hrs. Lipase AY 30 was immobilized in the same manner except that the protein solution was adjusted to pH 7.0 with sodium phosphate.

Enzyme and Solvent Screening for SOA Deacetylation. A scintillation vial was charged successively with 100 mg of powdered enzyme as received or prepared as described and 1.0 ml of 20 mM sucrose octaacetate (SOA) dissolved in an organic solvent. Following a 5 sec sonication, the vial was incubated in a controlled-temperature shaker at 45° C. and 300 RPM for 24 hrs. A 200 μl aliquot of the reaction mixture was withdrawn and centrifuged. The supernatant was collected and evaporated under a stream of $N_2$. The residue was reconstituted in 200 μl of acetonitrile and 10 μl of this solution was analyzed by HPLC.

Synthesis of Sucrose Heptaacetates by Enzymatic Deacetylation of SOA

Method A (proleather, lipase type II, lipase AP 12, SP-435 lipase or alcalase): SOA 0,203 g (0.3mmol) was dissolved in 15 ml diisopropyl ether and 1.5 g of the hydrolytic enzyme was added. The reaction mixture was sonicated (5 sec.) and placed in a rotatory shaker set at 45° C. and 300 RPM for 6 days. The enzyme was removed by filtration and washed with acetonitrile. The combined filtrate/washes were evaporated under reduced pressure and the residue chromatographed on a silica gel column (23×2.5 cm) using hexane/ethyl acetate (⅔) as eluant. Evaporation afforded 40 mg (alcalase), 39 mg (lipase type II), 34 mg (lipase AP 12), 11 mg (SP-435 lipase) and 60 mg (proleather) of the corresponding sucrose heptaacetates, respectively. Method B (lipase AY 30): SOA 0.170 g (0.25 mmol) was dissolved in 5 ml of t-butyl methyl ether and 0.5 g of lipase AY 30 was added. The reaction mixture was treated under the same conditions and workup as in method A to produce 43 mg of sucrose heptaacetates.

6-PAS Synthesis: Deacetylation of SOA with Alcalase in Diisopropyl Ether. SOA (1.35 g, 2mmol) was dissolved in 100 ml diisopropyl ether. To this solution, alcalase (10 g, precipitated from pH 9 buffer) was added. Following a 5 sec. sonication, the reaction mixture shaken at 45° C. and 300 RPM for 4 days. The enzyme was removed by filtration and washed with acetonitrile (100ml). The combined filtrate and washes were evaporated under reduced pressure and the residue chromatographed on a silica gel column (23×2.5 cm). Elution with hexane/ethyl acetate (⅔) afforded 360 mg of a mixture (1/7) of 2,3,4,6,1′,3′,4′- and 2,3,4,6,3′,4′,6′-hepta-O-acetyl sucrose. Continued elution with hexane/ethyl acetate (¼) yielded 86 mg of 2,3,4,6,3′,4′-hexa-O-acetyl sucrose Finally, elution with 500 ml ethyl acetate afforded 40 mg of a mixture of 4-PAS and 6-PAS. The sucrose pentaacetates were purified by silica gel chromatography (10×2.5 cm) eluting with hexane/ethyl acetate (1/9) to yield 5 mg of 6-PAS.

6-PAS Synthesis: Deacetylation of SOA Catalyzed by Proleather in Diisopropyl Ether Containing Methanol. SOA (1.35 g, 2 mmol) was dissolved in 100 ml diisopropyl ether containing 1M methanol. To this solution, proleather (5 g, precipitated from pH 10 buffer) was added. Following a 5 sec. sonication, the reaction mixture shaken at 45° C. and 300 RPM. After 2 days, 5 g proleather were added and the mixture shaken for 3 more days. The enzyme was removed by filtration and washed with acetonitrile (100 ml). The combined filtrate and washes were evaporated under reduced pressure and the residue chromatographed on a silica gel column (23×2.5 cm). Elution with hexane/ethyl acetate (⅔) afforded 579 mg of a mixture (1/7) of 2,3,4,6,1′,3′,4′- and 2,3,4,6,3′,4′,6′-hepta-O-acetyl sucrose. Continued elution with hexane/ethyl acetate (¼) yielded-205 mg of 2,3,4,6,3′,4′-hexa-O-acetyl sucrose.

Finally, elution with 500 ml ethyl acetate afforded 86 mg of a mixture of sucrose pentaacetates. The sucrose pentaacetates were purified by silica gel chromatography (10×2.5 cm) eluting with hexane/ethyl acetate (1/9) to yield 24 mg of 6-PAS.

6-PAS Synthesis: Lipase AP 12 Catalyzed Deacetylation of 2,3,4,6,3',4'-hexa-O-acetyl sucrose in Diisopropyl Ether 2,3,4,6,3',4'-hexa-O-acetyl sucrose (0.055 g, 0.092 mmol) was dissolved in 8 ml diisopropyl ether. Lipase AP 12 (0.8 g, precipitated from pH 6 buffer) was added to the solution. Following a 5 sec. sonication, the reaction mixture was shaken at 45° C. and 300 RPM for 20 hours. The enzyme was removed by filtration and washed with acetonitrile. The combined filtrate/washes were evaporated under reduced pressure and the residue chromatographed on a silica gel column (10×2.5 cm) eluting with hexane/ethyl acetate (1/9) to yield 5 mg of 6-PAS.

Nucleophile screening for alcalase, proleather or lipase AP 12 catalyzed deacetylation of SOA. A scintillation vial was charged successively with 100 mg of powdered enzyme prepared as described, 1.0 ml of 20 mM sucrose octaacetate (SOA) and 200 mM of the nucleophile dissolved in diisopropyl ether. Following a 5 sec sonication, the vial was incubated in a controlled-temperature shaker at 45° C. and 300 RPM for 66 hrs. A 200 µl aliquot of the reaction mixture was withdrawn and centrifuged. The supernatant was collected and evaporated under a stream of $N_2$. The residue was reconstituted in 200 µl of acetonitrile and 10 µl of this solution was analyzed by HPLC. For screening concentration effects on enzyme activity, the same protocol was followed except the nucleophile concentration was varied from 0 to 2000 mM.

Synthesis of sucrose octapropionate (SOP). A suspension of 10.27 g (30.0 mmol) of sucrose in 100 ml of pyridine was stirred and heated to reflux. After ca 75 min, an opaque solution with a small amount of undissolved sucrose was obtained which was cooled to ambient temperature and treated with 46.9 ml (362.7 mmol, 51% excess) of propionic anhydride in one portion. After an initial exotherm to 45°-46° C., the reaction mixture was stirred at ambient temperature for 19 hours. TLC analysis (silica gel, diethyl ether/acetone, 4/1) indicated the reaction was complete. The mixture was evaporated in vacuo to leave a syrup which was dissolved in toluene and re-evaporated 3 times to remove as much pyridine as possible. Residual pyridine and/or propionic acid was removed by dissolving the syrup in 100 ml of methylene chloride and washing successively 25 ml of water, 100 ml of 1% $NaHCO_3$ and 25 ml of water. After drying over $MgSO_4$ and filtration, the methylene chloride was evaporated to leave a nearly colorless syrup which slowly crystallized to a white waxy solid after several days at ambient temperature. HPLC analysis using a Supelcosil LC-18-DB reversed phase column and isocratic elution with 60/40 acetonitrile/water showed a $R_t=22.9$ min with purity estimated at 98.6%. Analysis for $C_{36}H_{54}O_{19}$: Theory C: 54.68; H: 6.88; Found C: 54.23; H: 6.80.

Enzyme screening for SOP deacylation in heptane. A scintillation vial was charged successively with 100 mg of powdered enzyme as received or prepared as described and 1.0 ml of 20 mM sucrose octapropionate (SOP) and 200 mM butanol dissolved in an organic solvent. Following a 5 sec sonication, the vial was incubated in a controlled-temperature shaker at 45° C. and 300 RPM for 24 hrs. A 200 µl aliquot of the reaction mixture was withdrawn and centrifuged. The supernatant was collected and 10 µl of this solution was analyzed by HPLC.

Solvent screening for SOP deacylation. A scintillation vial was charged successively with 100 mg of lipase AY 30 or protease type XXIII as described and 1.0 ml of 20 mM sucrose octapropionate (SOP) and 200mM butanol dissolved in an organic solvent. Following a 5 sec sonication, the vial was incubated in a controlled-temperature shaker at 45° C. and 300 RPM for 24 hrs. A 200 µl aliquot of the reaction mixture was withdrawn and centrifuged. The supernatant was collected and evaporated under a stream of $N_2$. The residue was reconstituted in 200 µl of acetonitrile and 10 µl of this solution was analyzed by HPLC.

As used herein, the terms "a sucrose 1'-acetate", "a sucrose 4'-acetate", "a sucrose 6'-acetate", "a sucrose 4-acetate", and "a sucrose 6-acetate" refer to octa-, hepta- or hexa-O-acetyl sucroses wherein the indicated position contains an acetyl substituent, the location of the remaining acetyl substituents being unspecified.

What is claimed is:

1. A process for the preparation of partially acylated derivatives of sucrose by the enzyme catalyzed deacylation of sucrose esters having at least 6 ester groups, wherein said process comprises treating a sucrose ester selected from the group consisting of sucrose octaacylate, sucrose heptaacylate and sucrose hexaacylate in a reaction medium comprising an organic solvent capable of dissolving the sucrose ester, with a hydrolytic enzyme or combination of hydrolytic enzymes capable of catalyzing the deacylation of said sucrose ester to produce a partially deacylated sucrose derivative having at least one more free hydroxyl group than the starting sucrose ester in a preselected position or positions, and recovering the resulting partially deacylated sucrose derivative, wherein, excluding water bound to said enzyme, said reaction medium contains not more than about 1 volume percent water, based on the volume of said organic solvent, provided that when said organic solvent is a water-immiscible compound, said reaction medium is monophasic.

2. The process of claim 1 wherein the sucrose ester is a sucrose alkanoate, a sucrose α-haloalkanoate, or a sucrose trihaloalkanoate wherein the alkanoate moiety has up to eight carbon atoms.

3. The process of claim 2 wherein the sucrose ester is selected from the group consisting of sucrose acetates, sucrose propionates, sucrose n- or sec-butyrates, sucrose chloroacetates, sucrose fluoroacetates, sucrose trichloroacetates and sucrose trifluoroacetates.

4. The process of claim 3 wherein the sucrose ester is sucrose octaacetate, sucrose heptaacetate, sucrose hexaacetate, sucrose octapropionate, sucrose heptapropionate or sucrose hexapropionate.

5. The process of claim 1 wherein the enzyme is a lipase, protease, esterase or amylase.

6. The process of claim 5 wherein the enzyme is selected from the group consisting of lipase AY 30, SP-435 lipase, protease N, lipase type II, alcalase, proleather, lipase AP 12, protease type XXIII, protease M, lipase type VII, protease type XIII, biozyme S, protease 2A, lipase CE, PC lipase, and MM lipase.

7. The process of claim 1 wherein the organic solvent is a hydrocarbon, an ether, a ketone, an ester, an alcohol, or a halogenated hydrocarbon.

8. The process of claim 7 wherein the organic solvent is a member selected from the group consisting of toluene, diisopropyl ether, carbon tetrachloride, ethylene glycol dimethyl and diethyl ether, di-n-butyl ether, acetonitrile, acetone, THF, cyclohexanone, 2-methyl THF, t-butyl methyl and ethyl ether, 2,5-dimethyl THF, cyclohexanol, n-butyl acetate, t-butyl acetate, 3-heptanone, methyl isobutyl ketone, di-n-propyl ether, butyl ethyl ether, t-amyl methyl ether, chloroform, benzene, anisole, phenetole, hexane, heptane, octane and cyclohexane.

9. The process of claim 8 wherein the organic solvent is diisopropyl ether, ethylene glycol diethyl ether, t-butyl methyl ether, 3-heptanone, dipropyl ether, butyl ethyl ether, t-amyl methyl ether, chloroform, 2,2,5,5-tetramethyl THF, toluene, carbon tetrachloride, n-butyl acetate, benzene, anisole.

10. The process of claim 1 wherein the reaction medium also contains an organic nucleophile wherein the nucleophile is a member selected from the group consisting of alcohols, amines, aminoalcohols, thiols, and oximes.

11. The process of claim 10 wherein the nucleophile is a member selected from the group consisting of methanol, ethanol, propanol, butanol, benzyl alcohol, cyclohexylmethanol, phenethyl alcohol, and diisopropylamine.

12. The process of claim 11 wherein the nucleophile is methanol, n-butanol, diisopropylamine, or phenethyl alcohol.

13. The process of claim 1 which comprises the concurrent or sequential treatment of sucrose octaacetate by a combination of enzymes selected from the group consisting of SP-435 lipase, protease N, alcalase, proleather, lipase AP 12, said combination being selected to deacetylate the ester groups on the 4-, 1'- and 6'- positions or on the 6-, 1'- and 6'- positions of the sucrose octaacetate, and recovering the 6,2,3,3',4'-penta-O-acetylsucrose or 4,2,3,3',4'-penta-O-acetylsucrose or both thus produced.

14. The process of claim 1 which comprises the treatment of a sucrose 1'-acetate with alcalase to deacetylate the ester group at the 1'- position.

15. The process of claim 1 which comprises the treatment of a sucrose 1'-acetate with proleather to deacetylate the ester group at the 1'- position.

16. The process of claim 1 which comprises the treatment of a sucrose 1'-acetate with protease N to deacetylate the ester group at the 1'- position.

17. The process of claim 1 which comprises the treatment of a sucrose 4'-acetate with protease N to deacetylate the ester group at the 4'- position.

18. The process of claim 1 which comprises the treatment of a sucrose 6'-acetate with protease N to deacetylate the ester group at the 6'- position.

19. The process of claim 1 which comprises the treatment of a sucrose 1'-acetate with lipase AY 30 to deacetylate the ester group at the 1'- position.

20. The process of claim 1 which comprises the treatment of a sucrose 4'-acetate with lipase AY 30 to deacetylate the ester group at the 4'- position.

21. The process of claim 1 which comprises the treatment of a sucrose 6'-acetate with SP-435 lipase to deacetylate the ester group at the 6'- position.

22. The process of claim 1 which comprises the treatment of a sucrose 4-acetate with lipase AP 12 to deacetylate the ester group at the 4- position.

23. The process of claim 1 which comprises the treatment of a sucrose 6-acetate with lipase AP 12 to deacetylate the ester group at the 6- position.

24. The process of claim 1 which comprises the steps of:
(a) the treatment of sucrose octaacetate with alcalase or proleather to produce a mixture of 2,3,4,6,1',3',4'-hepta-O-acetyl sucrose and 2,3,4,6,3',4',6'-hepta-O-acetyl sucrose; and
(b) the treatment of the product of step (a) with alcalase or proleather to produce 2,3,4,6,3',4'-hexa-O-acetyl sucrose.

25. The process of claim 24 wherein the product of step (b) is further treated with alcalase or proleather to produce 2,3,6,3',4'-penta-O-acetyl sucrose and 2,3,4,3',4'-penta-O-acetyl sucrose.

26. The process of claim 24 wherein the product of step (b) is further treated with lipase AP 12 to produce 2,3,6,3',4'-penta-O-acetyl sucrose and 2,3,4,3',4'-penta-O-acetyl sucrose.

27. The process of claim 24 wherein the organic solvent is an ether.

28. The process of claim 25 wherein the organic solvent is an ether.

29. The process of claim 26 wherein the organic solvent is an ether.

30. The process of claim 27 wherein the reaction medium is a mixture of an ether and an alcohol.

31. The process of claim 28 wherein the reaction medium is a mixture of an ether and an alcohol.

32. The process of claim 29 wherein the reaction medium is a mixture of an ether and an alcohol.

33. The process of claim 1 which comprises the treatment of a sucrose 6'-acetate with alcalase to deacetylate the ester group at the 6'-position.

34. The process of claim 1 which comprises the treatment of a sucrose 6'-acetate with proleather to deacetylate the ester group at the 6'-position.

35. The process of claim 1 which comprises the treatment of a sucrose 4'-acetate with lipase type II to deacetylate the ester group at the 4'-position.

* * * * *